United States Patent [19]

Jones

[11] 4,082,789

[45] Apr. 4, 1978

[54] PROSTAGLANDINS C$_2$

[75] Inventor: Robert L. Jones, Edinburgh, Scotland

[73] Assignee: The University Court of the University of Edinburgh, Edinburgh, Scotland

[21] Appl. No.: 662,637

[22] Filed: Mar. 1, 1976

Related U.S. Application Data

[63] Continuation of Ser. No. 510,076, Sep. 27, 1974, abandoned, which is a continuation of Ser. No. 345,347, Mar. 27, 1973, abandoned.

[30] Foreign Application Priority Data

Mar. 28, 1972 United Kingdom .............. 14520/72
May 17, 1972 United Kingdom .............. 23135/72

[51] Int. Cl.$^2$ ..................... C07C 177/00; C11C 1/00
[52] U.S. Cl. ..................................... 560/121; 195/30; 260/410.9 R; 260/413; 260/514 D; 424/305; 424/317
[58] Field of Search .......... 260/468 D, 514 D, 514 C, 260/514 A, 410, 410.5, 410.9 R, 413

[56] References Cited

U.S. PATENT DOCUMENTS 3,816,393 6/1974 Hayashi et al. ...................... 260/209

FOREIGN PATENT DOCUMENTS 2,128,674 12/1971 Germany ............................. 260/468

OTHER PUBLICATIONS

March, Advanced Organic Chemistry, p. 739 (1968).
N.Y. Academy of Science, 180, 73 (1971).

Primary Examiner—Robert Gerstl

[57] ABSTRACT

This invention is a group of prostaglandin-like compounds of the formula:

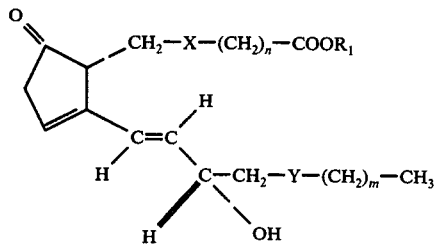

wherein $m$ is 0, 1, 2, or 3 and $n$ is 2, 3, 4, or 5, wherein X and Y are —CH$_2$CH$_2$— or X is cis—CH=CH— and Y is —CH$_2$CH$_2$— or cis—CH=CH—, and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, and the pharmacologically acceptable salts thereof when R$_1$ is hydrogen. These compounds are useful as vasodepressors and antisecretory agents, and in managing cases of renal disfunction.

9 Claims, No Drawings

PROSTAGLANDINS C₂

This is a continuation of application Ser. No. 510,076, filed Sept. 27, 1974, and now abandoned, which was a continuation of application Ser. No. 345,347, filed Mar. 27, 1973 and now abandoned.

DESCRIPTION OF THE INVENTION

This invention relates to novel compositions of matter and to novel processes for making those. More specifically, this invention is concerned with novel optically active organic compounds of the formula:

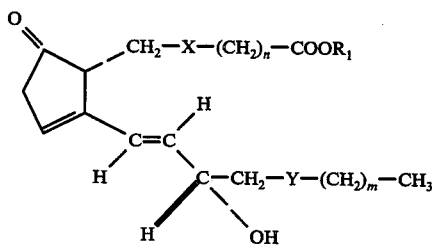

I wherein $m$ is 0, 1, 2, or 3 and $n$ is 2, 3, 4, or 5, wherein X and Y are —CH$_2$CH$_2$— or X is cis—CH=CH— and Y is —CH$_2$CH$_2$— or cis—CH=CH—, and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, and the pharmacologically acceptable salts thereof when R$_1$ is hydrogen.

Included within the scope of formula I wherein $m$ is one and $n$ is 3 are optically active compounds of the formulas:

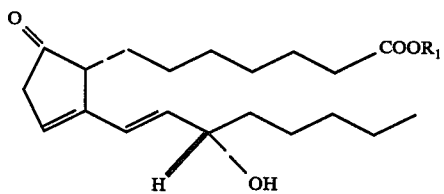

II

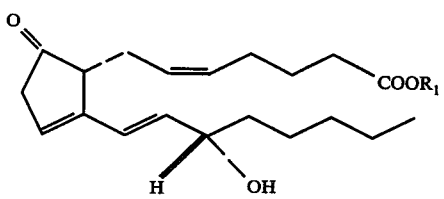

III

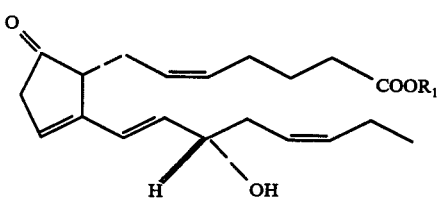

IV in formulas II, III, and IV, R$_1$ is as defined above.

This invention also relates to novel optically active compounds of the formula:

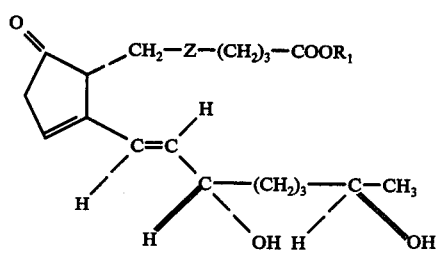

V wherein Z is —CH$_2$CH$_2$— or cis—CH=CH—, and wherein R$_1$ is as defined above, and pharmacologically acceptable salts thereof when R$_1$ is hydrogen.

Included within the scope of formula V are optically active compounds of the formulas:

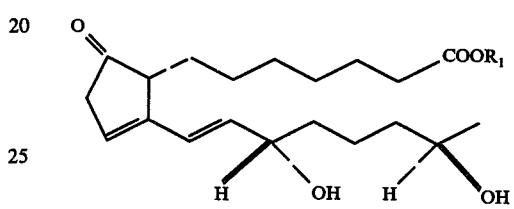

VI

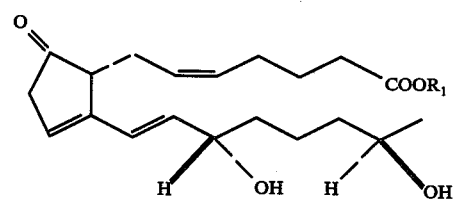

VII

In formulas VI and VII, R$_1$ is as defined above.

This invention also relates to novel optically active compounds of the formula:

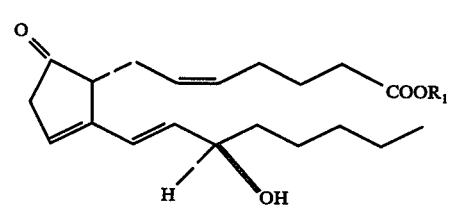

VIII wherein R$_1$ is as defined above, and pharmacologically acceptable salts thereof when R$_1$ is hydrogen.

The novel compounds of formulas I, II, III, IV, V, VI, VII, and VIII are related in structure to the substance known as prostanoic acid which has the formula and atom numbering:

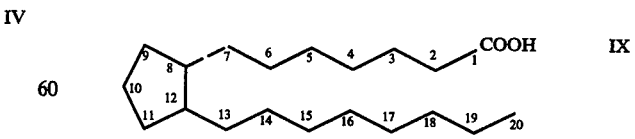

IX

There are various derivatives and derivative-analogs of prostanoic acid already known in the art. These are known as prostaglandins and prostaglandin analogs. For example, the compound known as prostaglandin E$_1$ (PGE$_1$) has the formula:

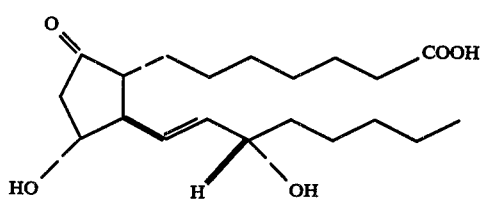

The compound known as prostaglandin E$_2$ (PGE$_2$) has the formula:

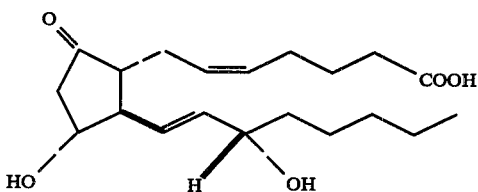

The compound known as prostaglandin E$_3$ (PGE$_3$) has the formula:

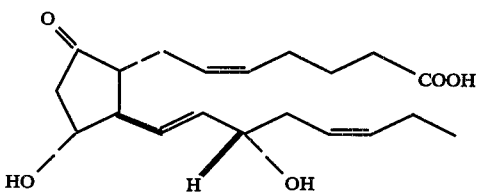

Compounds corresponding to PGE$_1$, PGE$_2$, and PGE$_3$ but without the ring hydroxy and with a carbon-carbon double bond between C-10 and C-11 in the ring are also known. These are named prostaglandins A (PGA). Thus, prostaglandin A$_1$ (PGA$_1$) has the formula:

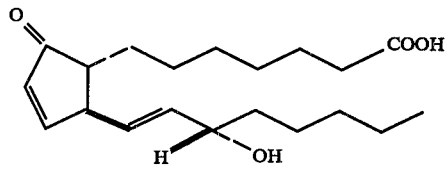

Prostaglandin A$_2$ (PGA$_2$) has the formula:

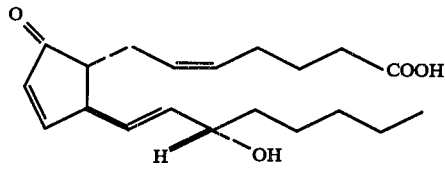

Prostaglandin A$_3$ (PGA$_3$) has the formula:

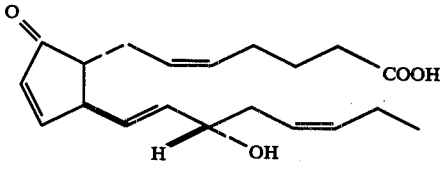

Compounds of formula I wherein $m$ is one and $n$ is 3, i.e., the compounds of formulas II, III, and IV, can be considered as derivatives of prostanoic acid, and can be named accordingly. Thus, the compound of formula II wherein R$_1$ is hydrogen has the name 15α-hydroxy-9-oxoprosta-11,trans-13-dienoic acid. The compound of formula III wherein R$_1$ is hydrogen has the name 15α-hydroxy-9-oxoprosta-cis-5,11,trans-13-trienoic acid. The compound of formula IV wherein R$_1$ is hydrogen has the name 15α-hydroxy-9-oxoprosta-cis-5,11,trans-13,-cis-17-tetraenoic acid.

For convenience, I have chosen to name the novel compounds of this invention as prostaglandins C, using the subscript numbers 1, 2, or 3 to designate the total number of carbon-carbon double bonds in the two side chains in accord with the PGE and PGA system of nomenclature. Thus, the novel compounds of formulas II, III, and IV wherein R$_1$ is hydrogen are named prostaglandin C$_1$ (PGC$_1$), prostaglandin C$_2$ (PGC$_2$), and prostaglandin C$_3$ (PGC$_3$), respectively.

The novel compounds encompassed by formula I wherein $m$ and $n$ are other than the combination of one for $m$ and 3 for $n$ are considered as analogs of the PGC compounds encompassed by formula I and are named with the use of prefixes to the corresponding PGC name. These prefixes are as follows:

| m | prefix |
|---|---|
| 0 | 20-nor |
| 2 | 20-methyl |
| 3 | 20-ethyl |
| n | prefix |
| 2 | 2-nor |
| 4 | 2a-homo |
| 5 | 2a,2b-dihomo |

Thus, the compounds of formula I wherein R$_1$ is hydrogen are named as follows for the various combinations of $m$ and $n$:

| m | n | name |
|---|---|---|
| 0 | 2 | 2,20-dinor-PGC |
| 1 | 2 | 2-nor-PGC |
| 2 | 2 | 2-nor-20-methyl-PGC |
| 3 | 2 | 2-nor-20-ethyl-PGC |
| 0 | 3 | 20-nor-PGC |
| 1 | 3 | PGC |
| 2 | 3 | 20-methyl-PGC |
| 3 | 3 | 20-ethyl-PGC |
| 0 | 4 | 2a-homo-20-nor-PGC |
| 1 | 4 | 2a-homo-PGC |
| 2 | 4 | 2a-homo-20-methyl-PGC |
| 3 | 4 | 2a-homo-20-ethyl-PGC |
| 0 | 5 | 2a,2b-dihomo-20-nor-PGC |
| 1 | 5 | 2a,2b-dihomo-PGC |
| 2 | 5 | 2a,2b-dihomo-20-methyl-PGC |
| 3 | 5 | 2a,2b-dihomo-20-ethyl-PGC |

A subscript 1, 2, or 3 is then added to the name to indicate a total of one, two, or three carbon-carbon double bonds in the two side-chains.

Prostaglandins A corresponding to the novel compounds of formulas VI, VII, and VIII are also known in the art. They have the formulas:

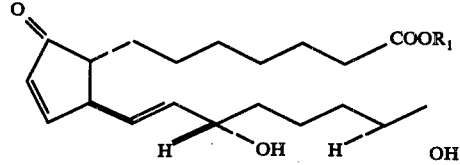

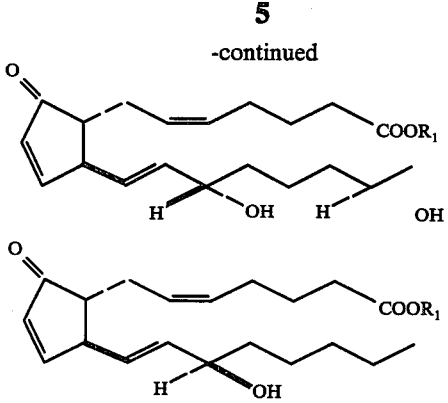

These compounds of formulas XVI, XVII, and XVIII are named 19-hydroxy-PGA$_1$, 19-hydroxy-PGA$_2$, and 15$\beta$-PGA$_2$, respectively. In accord with this nomenclature, the novel compounds of formulas VI, VII, and VIII wherein R$_1$ is hydrogen are named 19-hydroxy-PGC$_1$, 19-hydroxy-PGC$_2$, and 15$\beta$-PGC$_2$.

Molecules of the compounds encompassed by formulas I to XVIII above each have several centers of asymmetry. These formulas, including formulas I-VIII which represent the novel prostaglandin C compounds of this invention, are intended to represent optically active compounds each with the same absolute configuration as optically active prostaglandin E$_1$ (PGE$_1$) obtained from certain mammalian tissues, for example, sheep vesicular glands or human seminal plasma. See, for example, Bergstrom et al., J. Biol. Chem. 238, 3555 (1963), Horton, Experientia, 21, 113 (1965), Bergstrom et al. Pharmacol. Rev. 20, 1 (1968), and references cited in those.

In formulas I to XVIII, a broken line attachment to the cyclopentane ring indicates a chain in alpha configuration, i.e., below the plane of the cyclopentane ring. A heavy solid line attachment to the cyclopentane ring indicates a chain in beta configuration, i.e., above the plane of the cyclopentane ring. A regular solid line attachment to the cyclopentane ring indicates a planar configuration for that chain and the other attachments to the ring carbon atoms. The configuration for the side chain hydroxy in formulas I to IV and IX to XV is S although $\alpha$ is preferred as a designation for this configuration. The configurations for the two side chain hydroxy at C-15 and C-19 in formulas V, VI, VII, XVI, and XVII are S and R, respectively, although $\alpha$ and $\beta$, respectively, are preferred as designations for these configurations. The side chain hydroxy at C-15 in formulas VIII and XVIII is in R configuration. This configuration is also known as epi, although $\beta$ is preferred as a designation for the configuration. See Nature, 212, 38 (1966), Hamberg, European J. Biochem, 6, 147 (1968), and Weinheimer et al., Tetrahedron Letters 49, 5185 (1969), and references cited in those, for discussions of the stereochemistry of these prostaglandins.

The above-described known prostaglandins A, especially PGA$_1$ and PGA$_2$, are known to exhibit vasodepressor activity in laboratory animals prepared in various ways. See, for example, Horton et al., Br. J. Pharmoc. 37, 704 (1969); Weeks et al., J. Pharm. Pharmac. 21, 103 (1969); Higgins et al., Circulation Res. 28, 638 (1971); and Barner et al., J. Surg. Res. 12, 168 (1972). It has also been observed that PGA$_1$ increases renal blood flow, diuresis, and natruresis in laboratory animals, for example, when infused into the renal artery of dogs. See, for example, Weeks, Rush Presbyterian-St. Lukes Med. Bull. 9, 87 (1970), and references cited therein. See also Murphy et al., J. Surg. Res. 10, 533 (1970). Experiments in man also show that PGA$_1$ is useful in treating patients with essential hypertension and/or renal disfunction. See, for example, J. B. Lee et al., Ann. Int. Med. 74, 703 (1971); S. J. Lee et al., Kidney Int. 1, 254 (1972); Lee et al., Ann. N.Y. Acad. Sci., 180, 218 (1971); Fichman et al., Circ. Res. 31, Suppl. II, II-19 (1972); Westura et al., Circ. Res. 27, Suppl. I, I-131 (1970); and Carr, Ann. Intern. Med. 74, 830 (1971).

PGA$_1$ is also known to inhibit gastric secretion in man. See, for example, Wilson et al., Gastroenterology, 61, 201 (1971).

The novel formula I, II, III, IV, V, VI, VII, and VIII PGC compounds of this invention have qualitatively the same pharmacological properties described above for PGA$_1$ and PGA$_2$, and can be used for the same purposes and in the same manner described above. But quite surprisingly and completely unexpectedly, these novel PGC compounds are substantially more potent as pharmacological agents than the corresponding PGA compounds, especially with regard to vasodepressor activity, and for that reason, smaller amounts of the novel PGC compounds can be used to accomplish the desired pharmacological results.

It is perhaps relevant to point out that a mixture of substances said to contain a compound of the formula:

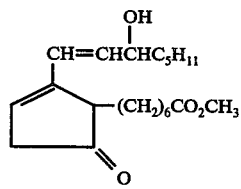

has been stated to cause a slight lowering in the blood pressure of the anesthetized rabbit. See U.S. Pat. No. 3,644,502. But this compound could not be separated from the other components of this mixture, and it is uncertain just what is in the mixture. Moreover, there is uncertainty with regard to the exact structure of this compound, for example, with regard to the stereochemical configuration of the attachments to the cyclopentane ring, the side chain hydroxy in the component which contains that, and the carbon-carbon double bond in the upper side chain. Moreover, in view of the manner in which this mixture was prepared, it is clear that all of the mixture components are optically inactive (racemic). For these reasons, this mixture would not be useful for the purposes described above for the novel PGC compounds of the present invention.

As described above, the novel PGC compounds of formulas I to VIII are used as hypotensive agents to reduce blood pressure in mammals, including man, especially in cases of essential hypertension. For this purpose and with particular regard to humans, the compounds are administered by intravenous infusion at the rate about 0.01 to about 50 $\mu$g. per kg. of body weight per minute, preferably at a rate about 0.1 to 5 $\mu$g. per kg. per minute, or in single or multiple intravenous doses of about 25 to 500 $\mu$g. per kg. of body weight total per day, the exact dose depending on the particular novel PGC used, on the age and weight of the subject, and on the severity of the hypertensive condition. The doses given herein are especially suitable for use of PGC$_1$ (formula II) and PGC$_2$ (formula III), and somewhat higher dose levels may be needed for some of the other novel PGC compounds of this invention. An appropriate dose range is readily determined for these other novel compounds by comparing the depressor activity of the particular compound with that of $PGC_1$ or $PGC_2$ in labratory animals, for example, by the procedures described in Weeks et al. or Horton et al., above cited.

As mentioned above, as for $PGA_1$, the novel PGC compounds of formulas I to VIII also increase the flow of blood in the mammalian kidney, thereby increasing volume and electrolyte content of the urine. For that reason, these novel PGC compounds are useful in managing cases of renal disfunction, especially those involving blockage of the renal vascular bed. Illustratively, the PGC compounds are useful to alleviate and correct cases of edema resulting, for example, from massive surface burns, and in the management of shock. For these purposes and with particular regard to humans, compounds are preferably first administered by intravenous injection at a dose in the range 10 to 1000 μg. per kg. of body weight, preferably in the range 100 to 500 μg. per kg. of body weight, or by intravenous infusion at a dose in the range 0.1 to 20 μg. per kg. of body weight per minute until the desired effect is obtained. Subsequent maintenance doses are given by intravenous injection or infusion, or intramuscular or subcutaneous injection in the total range 0.05 to 2 mg. per kg. of body weight per day. The doses given here are expecially suitable for $PGC_1$ and $PGC_2$.

As mentioned above, as for $PGA_1$, the novel PGC compounds of formulas I to VIII are useful in mammals, including man and certain useful animals, e.g., dogs and pigs, to reduce and control excessive gastric secretion, thereby reducing or avoiding gastrointestinal and duodenal ulcer formation, and accelerating the healing of such ulcers already present in the gastrointestinal and duodenal tracts. For this purpose, the compounds are injected or infused intravenously, subcutaneously, or intramuscularly in an infusion dose range about 0.1 μg. to about 500 μg. per kg. of body weight per minute, preferably in the range 1 to 50 μg. per kg. per minute, or in a total daily dose by injection or infusion in the range about 0.1 to about 20 mg. per kg. of body weight per day, or are administered orally in the range 0.1 to 50 mg. per kg. of body weight per day, the exact dose depending on the age, weight, and condition of the patient or animal, and on the frequency and route of administration.

For all of the above purposes, the novel formula I to VIII PGC compounds are used in free acid form, as esters, or in pharmacologically acceptable salt form.

When the ester form is used, any ester within the range of the above definition of $R_1$ is used. With regard to said definition, examples of alkyl of one to 12 carbon atoms, inclusive, are methyl, ethyl, propyl, butyl, pentyl, hexyl, heptyl, actyl, nonyl, decyl, undecyl, and dodecyl, and isomeric forms thereof, for example, isopropyl, sec. butyl, and 2-ethylhexyl. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Of these esters within the scope of $R_1$, it is preferred that the ester be alkyl of one to 4 carbon atoms, inclusive. Of those alkyl, methyl is especially preferred for optimum absorption by the animal body. The straight-chain octyl, nonyl, decyl, undecyl, and dodecyl esters are also especially preferred for prolonged activity in the animal body.

Pharmacologically acceptable salts of these novel PGC compounds useful for the purposes described above are those with pharmacologically accepatable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like, aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the novel compounds of formulas I to VIII are administered in various ways, e.g. intravenously, intramuscularly, or subcutaneously. For intravenous injection or infusion, sterile aqueous isotonic solutions are preferred. For subcutaneous or intramuscular injection, sterile solutions or suspensions in aqueous or non-aqueous media are used.

It is important when preparing the various novel PGC compounds of this invention as described hereinafter and in storing, formulating, dispensing, and administrating them, that they not be allowed contact with base and that solutions, especially aqueous solutions, containing them be maintained at a pH less than about 7, preferably in the pH range about 6 to 6.5. A basic environment results in a substantial and usually rapid decrease in biological activity of the PGC compound. This loss in activity occurs substantially more slowly in a neutral or midly acidic medium. If the storage or dispensing container is made of glass, the container should be washed with acid, e.g., acetic acid, before use. Although salts of the PGC compounds are suitably stable in solid form or in the absence of water or other polar solvents, solutions of the salt form should be buffered so that the pH of the solution is below about 7. The esters of these PGC compounds, especially the methyl esters, are somewhat more stable than the free acid or salt forms, and for that reason, these esters, especially the alkyl esters of one to 4 carbon atoms, inclusive, in the alkyl portion, and more especially the methyl esters, represent preferred embodiments of this inventions.

The novel PGC compounds of formulas I to VIII wherein $R_1$ is hydrogen are each prepared by incubating the corresponding PGA compound with the prostaglandin A isomerase enzyme of mammalian blood plasma at a pH about 6 to 7, preferably about 7. Thus, to prepare the novel PGC compounds of formula I, the PGA starting materials will have the formula:

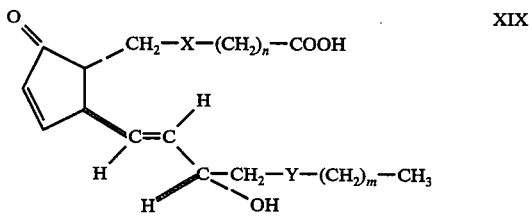
XIX wherein $m$ and $n$ are as defined above. Illustratively, $PGA_1$ is the starting material for the preparation of $PGC_1$ (formula II, $R_1$ is H), $PGA_2$ is the starting material for $PGC_2$ (formula III, $R_1$ is H), $PGA_3$ is the starting material for $PGC_3$ (formula IV, $R_1$ is H). With regard to the novel PGC compounds of formula V, VI, VII, and VIII 19-hydroxy-$PGA_1$ is the starting material for 19-hydroxy-$PGC_1$ (formula VI, $R_1$ is H), 19-hydroxy-$PGA_2$ is the starting material for 19-hydroxy-$PGC_2$ (formula VII, $R_1$ is H), and 15$\beta$-$PGA_2$ is the starting material for 15$\beta$-$PGC_2$ (formula VIII, $R_1$ is H).

$PGA_1$, $PGA_2$, $PGA_3$, 19-hydroxy-$PGA_1$, 19-hydroxy-$PGA_2$, and 15$\beta$-$PGA_2$ are all known in the art. The various PGA's encompassed by formula XVI other than $PGA_1$, $PGA_2$, and $PGA_3$ are also known in the art, or can be prepared by methods known in the art, for example, by dehydration of the corresponding PGEs all of which are known in the art. See, for example, the various PGEs disclosed in U.S. Pat. No. 3,636,120. See also, for example, Struijk et al., Rec. Trav. Chim. 85, 1233 (1966); French Pat. No. 2,115,086; and German Offenlegungsschrift 2,150,361. These dehydrations are carried out by methods known in the art for dehydration of other prostaglandins E. See, for example, Pike et al., Proc. Nobel Symposium II, Stockhoim (1966), Interscience Publishers, New York, pp. 162–163 (1967), and British Specification 1,097,533.

The prostaglandin A isomerase enzyme is known in the art, having been obtained in purified form from cat plasma. See Jones, Biochem. J. 119, 64P (1970), Horton et al., Ann, N. Y. Acad. Sci. 180, 351 (1971), and Jones, "The Pharmacology of Prostaglandins A and B", Thesis, the University of London (1970). As set forth in those references, this enzyme has previously been used to transform prostaglandin $A_1$ ($PGA_1$) to prostaglandin $B_1$ ($PGB_1$) which has the formula:

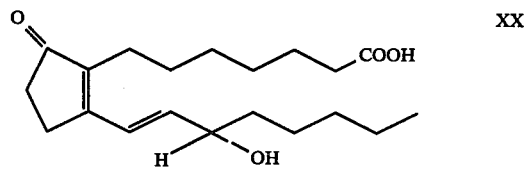
XX and which is substantially less active as a vasodepressor than $PGA_1$. The optimum pH for this apparently enzymatic isomerization was found to be about 8.5.

Now, I have made the surprising discovery that when $PGA_1$ is incubated with this same purified enzyme at a pH about 7, a different product is formed, namely $PGC_1$, a compound which, as described above, is substantially more active as a vasodepressor than $PGA_1$. Moreover, the other PGA-type compounds described above are also substrates for this same prostaglandin A isomerase enzyme, and PGC-type compounds are produced by incubation of each of the PGA-type compounds described above with the enzyme at a pH about 7.

The pH about 7 used for this enzymatic transformation of $PGA_2$ to PGC is an optimum pH, since at significantly higher pH values, the corresponding PGB is formed, presumably by isomerization of the initially-formed PGC, and at significantly lower pH values, the enzymatic conversion of PGA to PGC is inconveniently slower than at pH about 7.

A convenient temperature for the incubation of PGA-type compound with enzyme is about 25° C., although somewhat higher or lower temperatures, for example, the range about 20° to about 40° C., can also be used. At higher temperatures, for example, about 50° C. and above, the enzyme is deactivated.

The prostaglandin A isomerase enzyme can be obtained from the blood plasma of various mammalian species including rabbits, cats, pigs, dogs, and rats. This enzyme does not appear to be present in the blood plasma of oxen, sheep, guinea pigs, and humans.

Procedures for the preparation of the isomerase enzyme, procedures for incubation of PGA-type compounds with enzyme, and procedures for isolation and purification of the desired PGC-type product are set forth in the Preparations and Examples below.

The above-described enzymatic process produces PGC compounds in free acid form (formulas I to VII wherein $R_1$ is hydrogen). When an ester form within the scope of the above definition of $R_1$ is desired, the free acid is transformed to the desired ester by procedures known in the art. For example, esterification is readily accomplished by interaction of the free acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactant with the diazohydrocarbon be no longer than necessary to effect the desired esterification, preferably about one to about ten minutes, to avoid undesired molecular changes. Diazohydrocarbons are known in the art or are prepared by methods known in the art. See, for example, Organic Reactions, John Wiley & Sons, Inc., New York, N. Y., Vol. 8, pp. 389–394 (1954).

An alternative method for esterification of the free acid forms of the PGCs prepared according to this invention comprises transformation of the acid to the corresponding silver salt followed by interaction of that salt with an alkyl iodide.

Examples of suitable iodides are methyl iodide, ethyl iodide, butyl iodide, isobutyl iodide, tert-butyl iodide, and the like. The silver salts are prepared by conventional methods, for example, by slowly neutralizing the acid with slightly less than the stoichiometric amount of cold dilute aqueous ammonia, and then adding the stoichiometric amount of silver nitrate.

Still another even more general prior art method for esterification of the novel PGC acids of this invention comprises slowly neutralizing the acid with slightly less than the stoichiometric amount of triethylamine, reacting the amine salt with p-toluenesulfonyl chloride, or isobutyl chloroformate, and then reacting the resulting mixed anhydride with an alcohol or phenol corresponding to the desired $R_1$ moiety.

The pharmacologically acceptable salts of the novel formula I to VIII PGC compounds of this invention are also prepared by conventional methods, care being taken that contact is avoided with aqueous and other polar solution environments with a pH above 7. Amine salts, especially salts with tertiary amines, are preferred for the above described pharmacological purposes.

The invention can be more fully understood by the following preparations and examples. For a discussion of "Sephadex" gels, see Porath, Nature, 218, 834 (1968).

Preparation 1 Prostaglandin A Isomerase Enzyme.

The procedure for this preparation is essentially that described in my above-cited doctoral dissertation, Jones, "The Pharmacology of Prostaglandins A and B", Thesis, The University of London (1970), and is set forth here for convenience.

A. Isolation

Two cats weighing 2.5 and 2.3 kg. are anesthetized with pentobarbitone sodium (35 mg./kg.) injected intraperitoneally. The trachea is cannulated. An external juglar vein and a common carotid artery are also cannulated. Two-thousand (2000) U/kg. heparin is injected. Isotonic phosphate buffer (pH 7.4; 100 ml.) is infused intravenously at 10 ml./min., and blood is simultaneously collected from the carotid artery. The blood is centrifuged at 2000 X g for 10 min., and the plasma removed.

The plasma is maintained at 20° C. and stirred mechanically. The required amount of ammonium sulfate for protein and enzyme precipitation is calculated using the nomogram of Dixon, Biochem. J. 54, 457 (1953). Ammonium sulfate is solid form is added to the plasma and the precipitation process allowed to proceed for 15 minutes. The solution is centrifuged at 4000 X g for 15 minutes. The supernatant is poured off, and the residue is dissolved in a small volume of 0.1 M phosphate buffer (pH 7.4). Twenty-five, 50, 75, and 100% ammonium sulfate fractions are thus obtained. The fractions are dialyzed against 0.1 M phosphate buffer (pH 7.4) for 15 hours to remove the ammonium sulfate.

B. Purification

By the assay procedure described below, about 82% of the isomerase enzyme in the cat plasma is present in the 50 to 75% ammonium sulfate fraction. Therefore, this fraction alone is used as a source of purified enzyme.

The cationic phosphate buffer of the dialysis residue is exchanged for an anionic Tris-HCl buffer. This is done by gel filtration. Sephadex G-50 fine (50 g.) is allowed to swell in excess Tris-HCl buffer (ionic strength (1) = 0.1; pH 7.0) for 3 hours, and is then packed into a column (3.5 × 50 cm.). The concentrate (8 ml.) of the 50 to 75% ammonium sulfate fraction is loaded on column and eluted with 0.1 M Tris-HCl buffer (1 = 0.1; pH 7.0) at 0.5 ml./min., collecting 15-minute samples. All samples containing protein as shown by ultraviolet absorption at 280 nm are combined.

Next, DEAE Sephadex A-50 (4 g.) is equilibrated with 0.1 M Tris-HCl buffer (1 = 0.1; pH 7.0) for 3 days at 25° C. The resultant gel is packed into a column (1.6 × 21 cm.), and buffer is poured through the column at 0.2 ml./min. for 12 hours. About 1/30 of the 50 to 75% ammonium sulfate fraction after treatment described above is loaded on the column, and the column is eluted with 0.1 M Tris-HCl buffer (pH 7.0) containing initially 0.05 M sodium chloride and rising linearly to 0.515 M sodium chloride after 24 hours; flow rate 0.2 ml./min.; fraction volume 10 ml. Eluate fractions 11, 12, and 13 are combined.

The enzyme in these combined eluate fractions is concentrated by adding Sephadex G-25 coarse (2.4 g.) to each of 10-ml. portions of the combined eluate fractions, and swelling is allowed to continue for 10 minutes. The gel is then packed into a sinter funnel with a Whatman No. 1 filter disc, and centrifuged at 300 × g for 5 minutes. This same process is repeated on the filtrate, and the concentrated filtrate is retained.

Sephadex G-200 (5 g.) is swollen in 0.1 M Tris-HCl (pH 7.0) buffer containing 1 M sodium chloride for 3 days. The gel is then loaded into a column (1.6 × 60 cm.). the gel is allowed 3 days to settle, buffer being pumped through at a rate of 0.1 ml./min. About one-quarter of the concentrated filtrate from above is mixed with 1.6 ml. of the starting buffer, and the column is eluted with starting buffer containing 1.0 M sodium chloride; flow rate 0.21 ml./min.; fraction volume 3 ml. Eluate fractions 21, 22, 23, and 24 are combined to give a purified concentrated prostaglandin A isomerase enzyme preparation which is stored in frozen form at −20° C. until needed.

It is desirable though not essential that the various chromatographic procedures described above be carried out in a cold room, advantageously at about 4° C. The final enzyme preparation, prepared as described above, is estimated to represent about a 40 to 50-fold purification over the original cat plasma.

C. Assay.

It is necessary to have some means of determining the amount of useful prostaglandin A isomerase enzyme in a particular enzyme preparation so that one will know how much of that particular preparation should be used to transform a PGA to a PGC according to the novel process of this invention. The amount of enzyme present in a preparation will vary according to several factors, including source of the plasma, precise details of the isolation and purification procedures, and age and storage conditions for the enzyme preparation. In my doctoral dissertation, above cited, it is disclosed that incubation of $PGA_1$ with the isomerase enzyme at pH 8.5 results in gradual formation of $PGB_1$. The latter prostaglandin shows a characteristic ultraviolet absorption at 283 nm, and the amount of $PGB_1$ formed from $PGA_1$ in a unit of time can easily be determined spectrophotometrically on small scale incubations. In said doctoral dissertation, a unit (U) of isomerase enzyme is defined as the amount which will cause formation of one micromole of $PGB_1$ per minute under the following conditions: end volume 3.0 ml.; buffer 0.1 M Tris-HCl; pH 8.5, temperature 45° C.; initial concentration of $PGA_1$, 5 μg/.ml. I now prefer to define a unit (U) of isomerase enzyme in the same manner but with a temperature of 25° C. and 0.2 μ mole of $PGA_1$ as the initial total amount of substrate.

For this analysis of enzyme content, a Pye Unicam SP.800 spectrophotometer is used. The cells are of 1-cm. path length and 3-ml. capacity, and are enclosed in a constant temperature cell housing (SP.874) maintained at 25° C. by water from an external thermostated bath. The enzyme preparation sample to be estimated is diluted with 0.1 M Tris-HCl buffer (pH 8.5) to a definite volume. Diluted sample (2.90 ml.) is pipetted into a cell which is placed in the sample beam. A spectrum versus air is recorded. If the absorbance at 280 nm due to protein is greater than 1.2, a further dilution of the sample is made.

A second cell containing 3.0 ml. of the same sample dilution is then placed in the reference beam, and a spectrum is recorded to insure that the two cells and their contents are adequately matched. The cell contents are allowed 10 minutes to reach thermal equilibrium, and then 100 μ l. of PGA solution in 0.1 M Tris-HCl buffer (pH 8.5; 150 μg./ml. of $PGA_1$) is added to the sample cell. Using a SP.825 Series 2 program controller, a spectrum is recorded between 250 and 325 nm 2 minutes after addition of the substrate, and then at 5 minute intervals for at least another 20 minutes. The recorded absorbance is scale-expanded 5-fold and recorded on a Servoscribe potentiometric recorder. The cell contents are only subjected to the inradiating beam during each scan.

By this procedure, the formation of $PGB_1$ results in an absorbance increase at 283 nm. The relationship between the increase in absorbance at 283 nm and time is linear for at least 20 minutes after addition of the $PGA_1$. The increase in absorbance from time zero to 20 minutes is measured and divided by 20 to give the average increase in absorbance per minute. If the average increase in absorbance at 283 nm is greater than 0.005, then the enzyme preparation is diluted further to give an average absorbance increase per minute below about 0.005.

Using 3-ml. cells of 1 cm. path length, and estimating the absorbance of $PGB_1$ in water at pH 8.5 to be about 27,000 to about 27,500, addition of one unit (U) of isomerase to the above system will result in an absorbance change of 9.0 to 9.2 per minute. For practical purposes, the addition of one milliunit (mU) of isomerase to the above system results in an absorbance change of 0.0090 to 0.0092 per minute. Thus, for example, if the total absorbance change after 20 minutes is 0.085, the average change per minute is 0.00425, and the amount of isomerase added to the spectrophotometric system is 0.00425/0.0091 or 0.47 mU. This value will enable simple calculation of mU of isomerase in any given quantity of a particular isomerase enzyme preparation, taking into account the dilutions made for the analysis.

Since my initial work with the isolation, purification, and analysis of the prostaglandin A isomerase enzyme of cat plasma, which is not part of the present invention, additional work along these lines has been carried out and published. See, for example, Jones et al., Biochim Biophys. Acta 280, 588 (1972). Prostaglandin A isomerase enzyme prepared as described above and as described in this Jones et al. article are both useful in transforming PGA-type compounds to the novel PGC-type compounds of this invention.

EXAMPLE 1 $PGC_1$

Prostaglandin $A_1$ (20 mg.; 0.06 mmole) in 4 ml. of methanol is added to 6 mU of prostaglandin A isomerase (from cat plasma) in 56 ml. of 0.1 M Tris-HCl buffer (pH 7.0). The temperature of the reaction mixture is maintained at 25° C. When the ultraviolet absorbance of the reaction mixture at 234 nm reaches a maximum (about 90 minutes), the reaction mixture is cooled to 0° C. and applied to a column (40 × 600 mm) of G-25 Sephadex gel maintained between 0° and 4° C., eluting with Tris-HCl buffer (pH 7.0) at 8 ml. per minute, collecting 24-ml. fractions. Ultraviolet spectra of fractions with elution volumes of 500-900 ml. are obtained, and those fractions with a significant absorbance at 234 nm are combined, acidified to pH 5.5 with hydrochloric acid, and partitioned twice with an equal volume of diethyl ether. The combined ether phases are washed with water and evaporated to dryness. The residue is then purified by reversed-phase partition chromatography on hydrophobic diatomaceous earth (hydrophobic Hyflo Super-Cel; 6.75 g.) using solvent system F55 (a two-phase system consisting of 165 parts of methanol, 135 parts of water, 45 parts of chloroform, and 5 parts of heptane, the heavier phase being applied to the Hyflo Super-Cel and the lighter phase being used as eluent), and flow rate 7 ml. per hour. The reactant $PGA_1$ is eluted first, followed closely by by-product $PGB_1$, both as shown by ultraviolet absorption of eluate fractions at 217 nm ($PGA_1$) and 278 nm ($PBG_1$) respectively. At about eluate volume 180 ml., the eluent (moving phase) is made less polar by addition of 10% methanol, and the elution continued. Subsequent eluate fractions showing significant absorption at 234 nm are combined and evaporated to dryness, and the residue suspended in hexane and stored at −20° C.

The above residue is subsequently applied as a band to a 5 × 20 cm. thin-layer chromatography plate coated with a 0.5 mm. layer of silica gel G. Authentic $PGA_1$ and $PGB_1$ and a small portion of the residue are applied as spots to a second plate. Both plates are developed simultaneously in the same tank, using the solvent system toluene-dioxane-acetic acid (50:30:1). The marker plate spots are visualized by spraying the plate with 10% phosphomolybdic acid in ethanol followed by heating at 110° C. for 10 minutes. The silica gel from the 0.38-0.44 $R_f$ zone of the preparative plate (containing the residue only) is removed and eluted with methanol. The methanol is diluted with 50 volumes of water and extracted with diethyl ether. The ether is evaporated to give 4.2 mg. of $PGC_1$ which is stored dry, under nitrogen, at −20° C. $PGC_1$ shows maximum ultraviolet absorption at 235 nm in hexane, and 234 nm in methanol and in water (pH 7.0); infrared absorption at 1260 and 800 cm$^{-1}$, and a broad absorption band between 1760 and 1680 cm$^{-1}$.

Following the procedure of Example 1 but using 30 mU of prostaglandin isomerase rather than 6 mU, and using 6.7 mg of PGA$_1$ in methanol rather than the amount used in Example 1, PGC$_1$ is obtained in substantially higher yield.

EXAMPLE 2 PGC$_2$

Following the general procedure of Example 1, PGA$_2$ and isomerase enzyme at final concentrations in 0.1 M Tris-HCl buffer (pH 7.0) of 100 μg./ml. for PGA$_2$ and 0.5 mU/ml. for the enzyme are incubated at 25° C. for 45 minutes. The ratio is 0.02 mM of PGA$_2$ and 30 mU of isomerase. The reaction mixture is cooled to 0° C., and filtered through Sephadex G-25 gel as in Example 1. The eluant from the gel column is acidified to pH 5.5 with hydrochloric acid, and then partitioned twice with equal volumes of diethyl ether. The combined ether phases are washed with water, dried over sodium sulphate, and evaporated to dryness. The residue is chromatographed by reversed-phase partition chromatography, using hydrophobic Hyflo Super-Cel as a support and solvent system F 60 (methanol:water:chloroform:heptane:acetic acid 180:120:45:5:2). An 8-gram column will hold 50 mg. of lipid, and the elution volumes of PGA$_2$, PGB$_2$, and PGC$_2$ are 75, 85, and 95 ml., respectively. PGA$_2$, PGB$_2$, and PGC$_2$ show ultraviolet absorption at about the same nm as PGA$_1$, PGB$_1$, and PGC$_1$, and this is used as in Example 1 to choose the appropriate eluate fractions for combining to obtain PGC$_2$. The combined PGC$_2$ fractions are evaporated to dryness to give PGC$_2$. For storage, the PGC$_2$ is dissolved in methanol, and the solution is maintained at −20° C. PGC$_2$ shows infrared absorption (CH$_2$Cl$_2$) at 2900, 2820, 1740, 1705, 1455, 1370, 1135, 1045, and 970 cm$^{-1}$, and ultraviolet absorption at 234 nm with a molar extinction coefficient of 20,600 in methanol.

EXAMPLE 3 PGC$_3$

Following the procedures of Examples 1 or 2, PGA$_3$ is transformed to PGC$_3$.

EXAMPLE 4 19-Hydroxy-PGC$_1$

Following the procedures of Examples 1 or 2, 19-hydroxy-PGA$_1$ is transformed to 19-hydroxy-PGC$_1$; ultraviolet absorption at 234 nm with shoulders at 228 and 242 nm.

EXAMPLE 5 19-Hydroxy-PGC$_2$

Following the procedures of Examples 1 or 2, 19-hydroxy-PGA$_2$ is transformed to 19-hydroxy-PGC$_2$.

EXAMPLE 6 15β-PGC$_2$

Following the procedures of Examples 1 or 2, 15β-PGA$_2$ is transformed to 15β-PGC$_2$; ultraviolet absorption at 234 nm with shoulders at 228 and 242 nm.

Also following the procedures of Examples 1 or 2, 20-nor-PGA$_1$, 20-methyl-PGA$_1$, 20-ethyl-PGA$_1$, 20-nor-PGA$_2$, 20-methyl-PGA$_2$, 20-ethyl-PGA$_2$, 2a-homo-20-methyl-PGA$_1$, 2a-homo-20-ethyl-PGA$_2$, 2a,2b-dihomo-PGA$_1$, 2a,2b-dihomo-20-methyl-PGA$_2$, 2a,2b-dihomo-20-ethyl-PGA$_2$, and 20-ethyl-PGA$_3$ are transformed to 20-nor-PGC$_1$, 20-methyl-PGC$_1$, 20-ethyl-PGC$_1$, 20-nor-PGC$_2$, 20-methyl-PGC$_2$, 20-ethyl-PGC$_2$, 2a-homo-20-methyl-PGC$_1$, 2a-homo-20-ethyl-PGC$_2$, 2a,2b-dihomo-PGC$_1$, 2a,2b-dihomo-20-methyl-PGC$_2$, 2a,2b-dihomo-20-ethyl-PGC$_2$, and 20-ethyl-PGC$_3$, respectively.

EXAMPLE 7 PGC$_2$ Methyl Ester

Diazomethane (excess) in diethyl ether is added to a diethyl ether solution of PGC$_2$ at 25° C. After the reaction is complete as shown by the absence of PGC$_2$ spots on TLC, the diethyl ether and excess diazomethane are removed under reduced pressure to give PGC$_2$ methyl ester; ultraviolet absorption at 234 nm with shoulder at 229 nm; infrared absorption (CH$_2$Cl$_2$) at 2900, 2810, 1720, 1450 w, 1380, 1240, and 1045 cm$^{-1}$; R$_f$ on silica gel TLC 0.55 (methanol-benzene 5-95), 0.58 (acetone-benzene 10-90), 0.71 (acetone-dichloromethane 4-96).

EXAMPLE 8 PGC$_1$ Methyl Ester

Following the procedure of Example 7, PGC$_1$ is reacted with diazomethane to give PGC$_1$ methyl ester.

EXAMPLE 9 PGC$_3$ Methyl Ester

Following the procedure of Example 7, PGC$_3$ is reacted with diazomethane to give PGC$_3$ methyl ester.

EXAMPLE 10 19-Hydroxy-PGC$_1$ Methyl Ester

Following the procedure of Example 7, 19-hydroxy-PGC$_1$ is reacted with diazomethane to give 19-hydroxy-PGC$_1$ methyl ester.

EXAMPLE 11 19-Hydroxy-PGC$_2$ Methyl Ester

Following the procedure of Example 7, 19-hydroxy-PGC$_2$ is reacted with diazomethane to give 19-hydroxy-PGC$_2$ methyl ester.

EXAMPLE 12 15β-PGC$_2$ Methyl Ester

Following the procedure of Example 7, 15β-PGC$_2$ is reacted with diazomethane to give 15β-PGC$_2$ methyl ester.

Following the procedure of Example 7, each of the PGC-type compounds recited after Example 6 are reacted with diazomethane to give the corresponding methyl ester.

I claim:

1. An optically active compound of the formula:

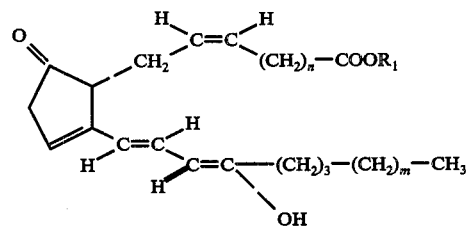

wherein m is 0, 1, 2, or 3 and n is 2, 3, 4, or 5, and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, and the pharmacologically acceptable salts thereof when R$_1$ is hydrogen.

2. An optically active compound of the formula:

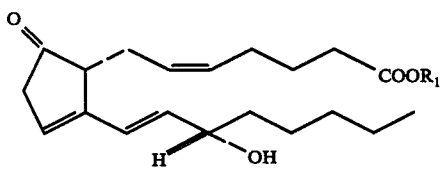

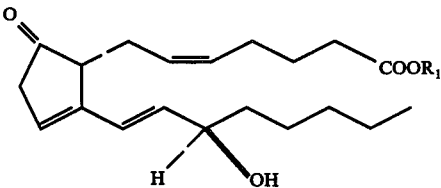

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, and the pharmacologically acceptable salts thereof when $R_1$ is hydrogen.

3. A compound according to claim 2 wherein $R_1$ is hydrogen or alkyl of one to 4 carbon atoms, inclusive, and pharmacologically acceptable salts thereof when $R_1$ is hydrogen.

4. A compound according to claim 2 wherein $R_1$ is hydrogen.

5. A compound according to claim 2 wherein $R_1$ is methyl.

6. An optically active compound of the formula:

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, and the pharmacologically acceptable salts thereof when $R_1$ is hydrogen.

7. A compound according to claim 6 wherein $R_1$ is hydrogen or alkyl of one to 4 carbon atoms, inclusive, and pharmacologically acceptable salts thereof when $R_1$ is hydrogen.

8. A compound according to claim 6 wherein $R_1$ is hydrogen.

9. A compound according to claim 6 wherein $R_1$ is methyl.

* * * * *